US006337564B2

(12) United States Patent
Manzini et al.

(10) Patent No.: US 6,337,564 B2
(45) Date of Patent: *Jan. 8, 2002

(54) DETECTING AND CLASSIFYING HARD AND SOFT INCLUSIONS IN LIQUID METAL

(75) Inventors: Richard A. Manzini, Greensburg; David H. De Young, Export, both of PA (US)

(73) Assignee: Alcoa Inc., Pittsburgh, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/290,597

(22) Filed: Apr. 13, 1999

(51) Int. Cl.[7] ............................................. G01N 27/00
(52) U.S. Cl. ..................................................... 324/71.4
(58) Field of Search ............................. 327/71.4, 71.1, 327/71.3, 450, 452; 356/72, 239.1, 335; 377/11

(56) References Cited

U.S. PATENT DOCUMENTS

| 4,555,662 A | 11/1985 | Doutre et al. ............... 324/71.4 |
| 4,600,880 A | 7/1986 | Doutre et al. ............... 324/71.4 |
| 4,763,065 A | 8/1988 | Hachey ....................... 324/71.4 |
| 5,039,935 A | 8/1991 | Hachey et al. .............. 324/71.4 |
| 5,130,639 A | 7/1992 | Hachey ....................... 324/71.4 |
| 5,198,749 A | 3/1993 | Guthrie et al. .............. 324/71.1 |
| 5,241,262 A | 8/1993 | Guthrie et al. .............. 324/71.1 |
| 5,584,578 A | 12/1996 | Clauss, Jr. ................... 374/140 |
| 5,834,928 A | * 11/1998 | Doutre ........................ 324/71.4 |

* cited by examiner

*Primary Examiner*—Safet Metjahic
*Assistant Examiner*—J Kerveros
(74) *Attorney, Agent, or Firm*—David W. Pearce-Smit; Douglas G. Glantz

(57) ABSTRACT

Apparatus and method for providing a classification of inclusions in molten metal. The apparatus and method include the steps of and means for obtaining an analog signal stream from a data collection apparatus, passing the analog signal stream through an analog to digital converter to convert the analog signal stream to a digital signal stream, and partitioning the digital signal stream into a discrete time frame of 5 milliseconds. The digital signal stream is vector normalized to provide a normalized signal stream having a largest amplitude magnitude of 1. The normalized signal stream is compared to a control of a prototype shape for determining a classification for the digital signal stream over the discrete time frame by decision logic to determine hard inclusions versus soft inclusions in the liquid metal. In one aspect, the normalized signal stream is passed through a decision module having at least one threshold unit and at least one digital logic table to make a decision of a soft, deformable inclusion or a hard inclusion. In one embodiment, the classification and size of the inclusions are counted in an histogram of classification and a histogram of size. The classification and size of the inclusions are viewed in a graphical user interface.

21 Claims, 3 Drawing Sheets

DETECTING AND CLASSIFYING HARD AND SOFT INCLUSIONS IN LIQUID METAL

BACKGROUND OF THE INVENTION

1. Technical Field

This invention relates to a method and apparatus for sensing inclusions in molten metal.

2. Background

Inclusions in molten or liquid metal are impurities found in the liquid metal. The presence of inclusions can affect the quality of ingots cast from that liquid metal. The quality of the ingot affects the quality of the subsequent sheet and plate products fabricated from that ingot.

High concentrations of inclusions in molten or liquid metal, e.g., such as inclusions in molten aluminum typically at sizes of 15 to 120 microns and in amounts over about three kilocounts per kilogram, adversely affect metal quality.

INTRODUCTION TO THE INVENTION

The impurities forming the inclusions in the liquid metal, in contrast to elemental impurities, are particles of separate phases suspended in the metal.

The inclusions in the liquid metal can be classified into one of two types of inclusions. The two types are hard and soft inclusions.

Hard inclusions primarily are attributable to oxides or other non-deformable particles. Examples of hard inclusions include magnesium oxide, aluminum oxide, spinel (magnesium aluminum oxide or $MgAl_2O_4$), silicon oxide, aluminum carbide, silicon carbide, titanium diboride, and vanadium diboride in certain circumstances.

The hard inclusions either come from the metal source itself, whether from ore or recycled metal, when it gets melted, or are created by oxidation during the melting process or elsewhere in the process because of oxygen present in the air or because of water vapor present, because of cascading or turbulence in the furnace, e.g., because of a fixed tap hole making for a lot of turbulence in the metal at the furnace outlet as liquid metal flows into the trough.

Oxide inclusions arise from the oxidation of aluminum or aluminum alloy at some point in its processing. Melting of scrap metal can result in oxide films, formed on the surface of the aluminum, being entrained in the molten metal. Alloying molten aluminum with magnesium can produce magnesium oxide inclusions from oxidation of the magnesium. Oxidation of molten metal as it flows through the launder system also can produce oxide inclusions. Turbulence at the molten metal surfaces and cascading of molten metal through air promote the formation of inclusions.

Aluminum carbide inclusions arise from the Hall-Heroult electrolytic cells in which primary aluminum is produced. Aluminum reacts with carbon cathodes in these cells to form aluminum carbide.

Silicon oxides arise from refractories used in furnaces, launder systems, and casting spouts.

Boride inclusions arise from grain refiners used to control the grain size in the solidified metal. Inclusions of borides would be a much larger size than boride particles that are effective as nucleating sites for aluminum grains.

Soft inclusions are attributable to molten salt droplets, gas bubbles, agglomerates of other very small particle types, or other deformable inclusions. Examples of soft inclusions include magnesium chloride, sodium chloride, potassium chloride, calcium chloride, aluminum chloride, cryolite salts, calcium fluoride, and liquid solutions containing these compounds or a combination of these compounds. Agglomerates of borides are another example of soft inclusions.

The soft inclusions come from using chlorine and chloride to treat the metal, e.g., in an in-line degassing process wherein even small amounts of chlorine gas form aluminum chloride and magnesium chloride. The aluminum chloride is not stable and tends to react to form magnesium chloride.

Fluxing molten metal with chlorine or a combination of an inert gas with chlorine removes hydrogen, alkali metals, alkaline earth metals, and hard inclusions from the molten metal.

Chlorine is used to react chemically with alkali and alkaline earth metals. The chlorine aids wetting of hard inclusions by flux gas bubbles and allows for removal by flotation. The chlorine aids the separation of skim from molten metal. The formation of molten chloride inclusions is a by-product of using chlorine to treat the metal. Fluxing is carried out in furnaces and in-line during the casting process.

The soft inclusions also come from using granular salts in the furnace, e.g., magnesium chloride, calcium chloride, sodium chloride, and potassium chloride, and combinations of magnesium chloride, calcium chloride, sodium chloride, and potassium chloride. These salts are used for reacting to remove sodium and calcium from the metal, to minimize melt loss, or to keep the furnace clean. Such granular salts in the furnace cause some carryover of molten salt inclusions.

The hard inclusions and soft inclusions range in size from about 1 micron to several hundred microns.

The total concentration of hard inclusions and soft inclusions is about 0.05–0.1 kilocount per kilogram, i.e., 50–100 particles per kilogram of metal, to about 150 kilocount per kilogram, i.e., 150,000 particles per kilogram of metal. The total concentration of hard inclusions and soft inclusions depends on the source of the metal from scrap type, solid primary metal, molten primary metal, or remelted beverage cans. The total concentration of hard inclusions and soft inclusions depends on settling time allowed in the furnace, the cleanliness of the furnace, the in-line treatment of the metal, the in-line filtration of the metal, and the design of the launder system.

Inclusions cause problems which depend on the type of product and the gauge of the product. For example, inclusions affect three inch plate differently from 6 micron thick foil. The inclusions will cause a hole or pinhole in the 6 micron thick foil. In beverage can or food can sheet, for example, pinholes are serious concerns.

Inclusions cause pinholes in foil and rigid container sheet such as food can sheet or beverage can sheet. Inclusions cause breakage of wire during drawing operations. Inclusions cause surface imperfections such as streaking in bright products such as reflector sheet or automobile trim. Inclusions also cause surface defects during extrusion processes. Inclusions also serve as nucleating sites for the formation of gas bubbles during solidification and thereby affect the fatigue life of certain products.

The two different inclusion types affect metal quality in different ways. It is difficult to know whether hard inclusions or soft inclusions cause particular problems because of an inability to distinguish between different inclusions.

Inclusions in the metal are analyzed by destructive methods of analysis. Currently, inclusions in the metal are analyzed and classified by destructive testing by taking a sample of the metal, solidifying the metal sample, cutting open the solid metal, looking at it under a microscope, and classifying or identifying the inclusion in the solid metal sample to determine qualitatively, and semi-quantitatively, whether the inclusion is a hard or soft inclusion.

Currently, inclusions in the molten metal are analyzed and classified by destructive testing by taking a sample of the molten metal and metallographically analyzing the sample for inclusions. The inclusions in the metal are concentrated in the sample by passing the molten metal through a filter or frit and then metallographically analyzing the sample to search for the inclusions at the leading edge of the filter or frit. Podfa and LAIS are trade marks of two commercially available sampling systems based on metallographic analysis. The metallographic analysis identifies the inclusion types and distinguishes between what are hard and soft inclusions at molten metal temperatures. However, the metallographic analysis is only semi-quantitative and does not provide results in real time.

Currently, inclusions in the metal are analyzed by non-destructive testing by ultrasonic testing. However, ultrasonic testing is performed only on the metal after it is solidified into a solid part. Moreover, ultrasonic testing provides a resolution of only about 1/64 inch. Much smaller inclusions cause problems in certain products. For example, a six micron diameter inclusion will cause a pinhole in 6 micron thick foil.

It is difficult to know from ultrasonic non-destructive testing on a solidified part whether an inclusion originated as a hard or soft inclusion. For example, it is sometimes difficult to know with certainty whether a processing problem is caused by a hard inclusion or hydrogen. In some cases, the inclusion may serve as nucleating sites for hydrogen bubbles. It would be highly advantageous to know, in real time, the identification and classification of the inclusion.

Current instrumentation technology for measuring inclusions in liquid metal streams does not discriminate between the two different types of inclusions. The current instrumentation technology does not identify whether the inclusions are hard or soft inclusions. The current method detects the existence of any inclusions and provides aggregate measures of inclusion concentrations and particle size.

Lumping together of inclusion types is undesirable because process operators and engineers prefer to know the type of inclusions in the liquid metal to determine the potential sources for the contamination and to determine ways to reduce or eliminate the harmful inclusions. Because the two inclusion types affect metal quality in different ways and because the two inclusion types are controlled in different ways, a method and apparatus are needed to discriminate and identify the two different types of inclusions.

A method and apparatus are needed to discriminate and classify or identify the two different types of inclusions in liquid metal streams in real time.

The ability to classify particle types in liquid metal streams in real time would enable the creation of guidelines on what to change in a continuous casting process in real time. The ability to classify particle types in liquid metal streams in real time would enable the creation of procedures to eliminate or reduce the influence of the inclusions on ingot quality in real time. For example, if a preponderance of salt particles (i.e., soft inclusion) is detected in real time, the guideline may be to reduce a chlorine rate in an on-going continuous casting process to optimize salt collector, to reduce a flux amount, or to add a filter. Improving the quality of cast ingot in this way would greatly improve the processing of products fabricated downstream from the continuous casting process.

A current instrument used for measuring inclusion concentrations employs a Coulter counter as a liquid stream passes through an orifice, using counter principles for its sensing element. By Coulter counter is meant a technique for counting pulses as a liquid stream passes through an orifice. A constant current is passed between electrodes on both sides of the orifice. As inclusion particles are drawn through a small orifice, and as a voltage between the electrodes increases, the electronic sensor produces exponentially-shaped voltage pulses. The voltage pulses have amplitudes which are a function of the effective particle diameter.

U.S. Pat. Nos. 4,555,662 and 4,600,880 to Doutre et al. disclose a method and apparatus, known as LiMCA for Liquid Metal Cleanliness Analyzer, for the detection of non-conductive particulates in molten aluminum, gallium, zinc and lead. A very small diameter passage into the container (about 300 micrometers for aluminum) forms a current path between two electrodes carrying a current of up to 500 amperes. The path is surrounded by liquid metal which forms a Faraday cage screening the path, enabling the passage of a particulate of about 15 micrometers or larger to produce a voltage pulse between the electrodes of greater than 5 microvolts, which is detectable above the background noise, which is of about that value.

U.S. Pat. No. 4,763,065 to Hachey discloses an apparatus for the detection and measurement of suspended particulates in a molten metal. A container composite wall includes concentric electrically conducting outer and inner walls (10) and (12) and a disc (14) of refractory material having a passage (16) of predetermined size. Molten metal is pumped through the passage (16) to establish a current path from the inner wall through the passage to the outer wall. A current is passed along the current path, and voltage changes are measured as indicating passage of suspended particulates through the passage.

U.S. Pat. No. 5,039,935 to Hachey discloses on-line particle determination in molten metals. A sample of molten metal is drawn by a vacuum through a calibrated passage in the side wall of a heat resistant tube while a current is established through the passage between two electrodes. The passage of non-conducting particles through the orifice produces pulses of magnitude and rate indicate respectively their size and the number of particles per unit volume. The electrodes and their leads form an interference-receiving antenna so that the wanted test signal, whose signal/noise ratio is inherently low, is subject to interference from neighboring sources, such as motors, fluorescent lamps and particularly induction furnaces. The patent discloses a cancellation signal to reduce the unwanted interference component in the test signal by a cancellation antenna.

U.S. Pat. No. 5,130,639 to Hachey discloses an apparatus for on-line particle determination in molten metals. A sample of molten metal is drawn through a calibrated passage while a steady current is established through the passage between two electrodes. Particles moving through the passage produce voltage pulses at a magnitude and rate to indicate size and number per unit volume. The wanted test signal is obtained between two current-carrying electrodes, or between two other electrodes disposed on opposite sides of the passage. The electrodes form an interference-receiving antenna so that the wanted low signal/noise ratio test signal is overlaid with interference from neighboring sources. This interference is reduced by a cancellation signal produced by a cancellation antenna constituted by a similar pair of electrodes, either separate from the main current-carrying electrodes or having one of them in common. A four electrode configuration permits the diameter of the passage to be monitored continuously. A five electrode configuration has three electrodes separate from the current-carrying electrodes forming the two antennae and connected differentially. A further electrode minimizes ground loops in the signal path. A head member carrying the tube and electrode cluster is mounted to move between operative and storage positions relative to a main body member carrying the power supply; these are made symmetrical about a longitudinal axis so that interference signals are in anti-phase and cancel.

U.S. Pat. No. 5,241,262 to Guthrie et al. discloses a molten metal inclusion sensor intended for "continuous" use in the testing of steel, i.e., a useful life of at least about 30 minutes. A probe detachably connected to a water-cooled support member (35) includes a tube (30) of heat resistant material, preferably silica, an inner electrode (31) mounted on its interior wall, and an outer electrode (32) mounted on its exterior wall. Molten metal enters the tube interior through an orifice (33) upon its immersion in the molten metal. The flow of metal with entrained inclusions is monitored by measuring the voltage between the electrodes (31, 32). The electrodes (31, 32) are preferably of graphite and are shaped to fit closely against the walls of the part of the tube (30) immersed in the metal and are of a material that retains enough mechanical strength to support the tube (30) as the metal is pumped into and out of the interior, the metal remaining hot enough for this pumping to occur. The orifice (33) is contoured to produce streamline flow and the Reynolds number of the flow preferably is kept below 2000.

U.S. Pat. No. 5,584,578 to Clauss, Jr. discloses a drop-in immersion probe for inserting into molten metal. A cylindrical measurement head has an axis and a first axial end inwardly tapered toward the axis. The measurement head is made of a combination of materials having a combined density greater than the density of the molten metal. A sensor element extends outwardly from the first axial end of the measurement head proximate the axis, and a slag cap covers the first end of the measurement head and the sensor element. Lead wire extends outwardly from the measurement head and has one end electrically connected to the sensor element. A portion of the lead wire extending outwardly from the measurement head is covered by a protective sleeve of heat-resistant material.

U.S. Pat. No. 5,198,749 to Guthrie et al. discloses a molten metal inclusion sensor. A single use disposable probe tube of heat resistant material has an inner electrode mounted on its interior wall and an outer electrode mounted on its exterior wall. The molten metal enters the tube interior through an orifice in its wall past a jet-preventer insert upon its immersion in the molten metal. The flow of metal with entrained inclusions is monitored by measuring the voltage between the electrodes. The Reynolds number of the flow is maintained below 2000. The tube interior is divided by a narrow bore into two compartments so that metal enters one compartment and freezes in the bore so that it cannot enter the second compartment, protecting the vacuum source and establishing the quantity of metal entering the probe. The orifice is closed by a meltable cover, and the cover is protected by a meltable shield to enable the probe to be passed through an overlying slag layer without entry of slag to the probe interior. The electrodes and the body of the probe should have a useful life in the bath of about 2 minutes.

It is an object of the present invention to discriminate and identify different types of inclusions in a liquid metal stream.

It is an object of the present invention to discriminate and identify different types of inclusions in a liquid metal stream in real time.

It is another object of the present invention to discriminate and identify between hard inclusions and soft inclusions in a liquid metal stream in real time.

It is another object of the present invention to discriminate and identify between hard inclusions and soft inclusions in a liquid metal stream in real time.

It is an object of the present invention to provide a realtime DSP (Digital Signal Processing) based pulse classification and peak detection method and apparatus for separating two distinct signal pulse classes from an analog signal stream.

It is an object of the present invention to provide updated histograms of the current distribution of amplitudes related to inclusion size, to maintain counts of each detected pulse type, and to compute a running probability of occurrence value for each of the pulses.

It is an object of the present invention to provide a displays and controls graphical user interface GUI screen to summarize data processed by the details of the algorithms and to present a visual display of the summarized data in a suitable operator interface.

These and other objects of the present invention will become apparent from reference to the figures of the drawings and the detailed description which follow.

SUMMARY OF THE INVENTION

The present invention provides an apparatus and method of determining a classification of inclusions in molten metal. The apparatus and method of the present invention include the steps of and means for obtaining an analog signal stream from a LiMCA data collection apparatus, passing the analog signal stream through an analog to digital converter to convert the analog signal stream to a digital signal stream, and partitioning the digital signal stream into discrete time frames or vector of 5 milliseconds length and sampled at a rate of 10 kHZ. The digital signal stream is normalized to provide a normalized signal vector, preferably, having a largest vector magnitude of 1. The normalized signal vector is compared to a control prototype shape for determining a classification for the digital signal vector over the discrete time frame by decision logic to determine hard inclusions versus soft inclusions in the liquid metal. In one aspect, the normalized signal vector is passed through a decision module having at least one threshold unit and at least one digital logic table to make a decision of a soft, deformable inclusion or a hard inclusion. In one embodiment of the present invention, the classification and size of the inclusions are counted in an histogram of classification and a histogram of size. The classification and size of the inclusions are viewed in a graphical user interface.

DETAILED DESCRIPTION

Figure 1:
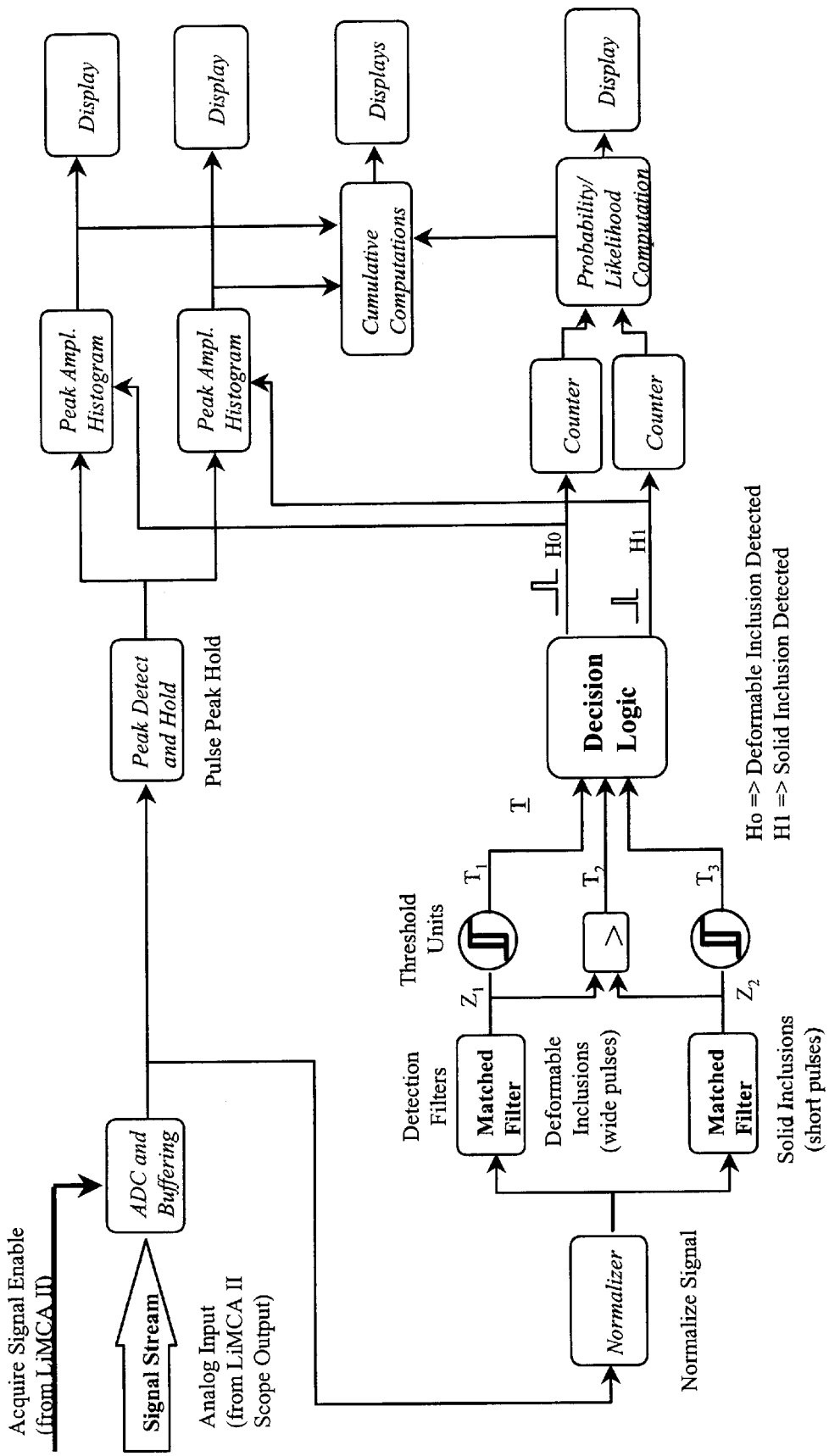
FIG. 1 is a process flow diagram for a inclusion particle detection and classifying apparatus and method of the present invention.

In accordance with the present invention, apparatus and method determine a classification of inclusions in molten metal. The apparatus and method of the present invention obtain an analog signal stream from a data collection apparatus, pass the analog signal stream through an analog to digital converter to convert the analog signal stream to a digital signal stream, and partitioning the digital signal stream into discrete time frames or vector of 5 milliseconds length and sampled at a rate of 10 kHZ. The digital signal stream is normalized to provide a normalized signal vector, preferably, a vector magnitude of 1. The normalized signal vector is compared to a control prototype shape for determining a classification for the digital signal vector over the discrete time frame by decision logic to determine hard inclusions versus soft inclusions in the liquid metal. In one aspect, the normalized signal vector is passed through a decision module having at least one threshold unit and at least one digital logic table to make a decision of a soft, deformable inclusion or a hard inclusion. In one embodiment of the present invention, the classification and size of the inclusions are counted in an histogram of classification and a histogram of size. The classification and size of the inclusions are viewed in a graphical user interface.

In accordance with the process and apparatus of the present invention, we have found that hard inclusions cause most of the specific problems, and soft inclusions cause particular problems of which are less harmful. In accordance with the process and apparatus of the present invention, we have found that hard inclusions cause most of the specific problems, because we have been able to distinguish the types of inclusions. In accordance with the process and apparatus of the present invention, we have found that inclusion defects in products turn out to contain solid inclusions.

The method and apparatus of the present invention provide a novel use of, and novel apparatus combination incorporating, an instrument measuring inclusion concentrations employing Coulter counter principles for its sensing element. As inclusion particles are drawn through a small orifice, an electronic sensor of the instrument measuring inclusion concentrations produces exponentially-shaped voltage pulses. The voltage pulses have amplitudes which are a function of the effective particle diameter.

The shape of the exponentially-shaped voltage pulses detected by the instrument measuring inclusion concentrations employing Coulter counter principles also contains information about the type of particle. Hard inclusions tend to have short pulse widths. Soft inclusions tend to have wide pulse widths. The instrument measuring inclusion concentrations employing Coulter counter principles does not distinguish between pulse shapes but only measures pulse amplitudes from which it computes inclusion size. It is this pulse stream that the method and apparatus of the present invention process to detect and classify the different inclusion types and sizes.

Referring now to FIG. 1, a process flow diagram is shown for a inclusion particle detection and classifying apparatus and method of the present invention.

The method and apparatus of the present invention employ on-line digital signal processing of the raw analog pulse stream from a LiMCA II instrument, available commercially from Bomem Inc., Quebec, Canada, to detect and classify inclusions.

The LiMCA machine and method are based on the Coulter counter principle for collecting data. A closed end glass tube containing a 300 $\mu$m diameter hole is immersed in molten aluminum. Through argon pressure and vacuum, metal is cycled in and out of the glass probe. During the fill portion of the cycle, a constant electrical current is applied between an electrode inside the tube and another electrode outside the tube, and the voltage between the two electrodes is monitored. A non-metallic inclusion passing through the orifice produces a voltage spike because the inclusion is less conductive than molten aluminum. The inclusion concentration is determined by counting the number of the spikes. The size of each inclusion is determined by measuring the magnitude of each voltage. While the principle of the LiMCA method is rather simple, the equipment is complex because the magnitudes of the voltage spikes are small, and rather sophisticated methods for minimizing and canceling electrical noise are required.

The inclusion size range covered by LiMCA is nominally 20 to 320 $\mu$m, although the maximum size that can be resolved is 140 $\mu$m. Particles in the 15 to 20 $\mu$m range are reported even though this size range can be prone to error from noise.

The method and apparatus of the present invention are based on the use of a set of digital matched filters for detecting the existence and shape of the inclusions. The outputs of the matched filters then are processed by decision logic algorithms that classify the inclusion as soft, hard, or neither. The matched filters are composed of a 2 orthonormal basis functions (signal space) constructed from two prototype (exemplar) pulse shape functions (vectors) of dimension 50. These vectors correspond to the representative hard and soft inclusion pulse shapes. The two prototype pulse shape vectors then are projected into this orthonormal signal space to obtain two, 50-dimensional reference vectors.

To create an input signal vector, the input pulse stream is sampled at 10 KHz (100 microsec) rate. A 5 millisecond wide sliding window or frame of the digitized pulse stream data then is normalized and projected onto the orthonormal signal space to obtain a 2-dimensional input vector in the reference space. The input vector then is compared against the two reference vectors using an inner product calculation. The results of the comparison then are processed by the decision logic, which decides what class, if any, the input pulse belongs to. Follow-up computations are performed to compute the particle size and distributions. All computational results are collected and stored to disk files and displayed on the interface screen.

LiMCA signal processing provides an analog voltage signal obtained from an instrument that measures inclusions in a molten aluminum metal stream. These inclusions represent impurities in the metal stream and are of two basic types: soft and hard. Hard inclusions are due to salt or metal aggregates while soft inclusions are typically due to gas bubbles. The amplitudes of these pulses are related to the size of the respective inclusion types. It is important to obtain the peak pulse amplitudes to compute and maintain an amplitude histogram that gives an indication of the distribution of inclusion sizes as the process is operating. In addition, it is important to obtain a probability estimate for each type of pulse based on the frequency of occurrence of each respective pulse type.

The present invention provides a realtime DSP based pulse classification and peak detection system for separating two distinct signal pulse classes from an analog signal stream.

The peak amplitudes of each classified pulse are used to update histograms that represent the current distribution of amplitudes that relate to inclusion size. Counts of each detected pulse type are maintained and used to compute a running probability of occurrence value for each of the pulses.

The present invention provides a displays and controls graphical user interface GUI screen to summarize data processed by the details of the algorithms and to present a visual display of the summarized data in a suitable operator interface.

The LiMCA Signal Processing extracts important information from the signal stream measured at the scope output connector of the LiMCA instrument. The voltage signal first is converted from continuous analog form to digital form using an Analog-to-Digital Converter (ADC). The ADC is used to collect samples on the analog stream at a rate of 10 kilohertz with 16 bits of resolution. The digitized output of the ADC then is stored in a buffer array in memory until the sampling interval of the LiMCA has completed. Upon completion of the sampling interval, analysis of the pulse signals in the buffer commences. After analysis and display of the results, the cycle repeats itself at approximately one minute cycles.

Upon completion of the sampling interval, analysis of the stored signals in buffer memory proceeds. Signal features of importance include the amplitude of the particle pulses and the shape of the particle pulses. To extract detailed information from these pulses downstream signal processing algorithms are then performed. The function of the downstream processing is (1) to determine particle size from pulse amplitude and (2) to classify particle type as hard or soft from pulse shape. This classification can be formulated as a statistical hypothesis test, wherein:

$H_0$: The pulse is undefinable or no inclusion present.
$H_1$: The pulse is due to a soft particle inclusion.
$H_2$: The pulse is due to a hard particle inclusion.

To classify the signal pulses, a vector space approach is employed which functions as a digital matched filter for each pulse class. A moving window of length 5 milliseconds is used to segment the signal stream into frames or vectors of length 50 samples (5e−3 secs*1/10e3). The signal vector $\underline{x}$ then is processed by the detection and classification logic to determine the nature of the pulse and to tally the total number of counts for the computed particle size, particle size being proportional to the measured pulse amplitude.

The classification process is initiated by first projecting each signal vector $\underline{x}$ onto a two-dimensional signal space S spanned by an orthogonal basis U={u1,u2} derived from the prototype vectors that represent the two pulse classes. A distance metric d for S, such as the inner product operation, then is used to determine which prototype is closest to the input vector $\underline{x}$. A normalizing unit is used to preprocess the signal vector $\underline{x}$ so that the norm of $\underline{x}=\|x\|$ equals unity. The purpose of the normalizer is to prevent the amplitude of $\underline{x}$ from overwhelming the inner product computation between the input signal vector and the class prototype as shown in Equation 1.

$$d=\{x,v\}=\|\underline{x}\|\|\underline{v}\|\cos\theta \quad \text{(Equation 1.)}$$

The important measure of similarity then becomes the cosine term, since both norms are equal to unity. Prototype vectors used to create the signal space U are obtained from actual pulse signal data obtained from the LiMCA instrument. Representative pulse signals for both the hard and soft particles are used to create the orthogonal basis vectors $u_1$ and $u_2$ that form U. The Gram-Schmidt orthonormalization procedure is used to create U from these data vectors. The data vectors are chosen for their shape characteristics that most commonly represent the concept of hard and soft particle types. After creating U, the representative class signal vectors then are projected onto U creating the class prototype vectors $v_1$ and $v_2$. The projection of the input vector onto U then is accomplished. The detection process performs the matched filter computation and proceeds to output the 2 filter outputs to the threshold and comparator units. The threshold units have binary output 0, if the match is less than a predetermined threshold, and 1 if the match is greater than or equal to the threshold. The comparator unit output a 1 if the wide pulse detection filter is greater than the narrow pulse detection filter, otherwise it outputs a 0. The binary vector from the threshold and comparator units then is passed to the decision logic unit for final determination of the pulse class from the current input frame. A binary lookup table is used to perform this function.

Figure 2:
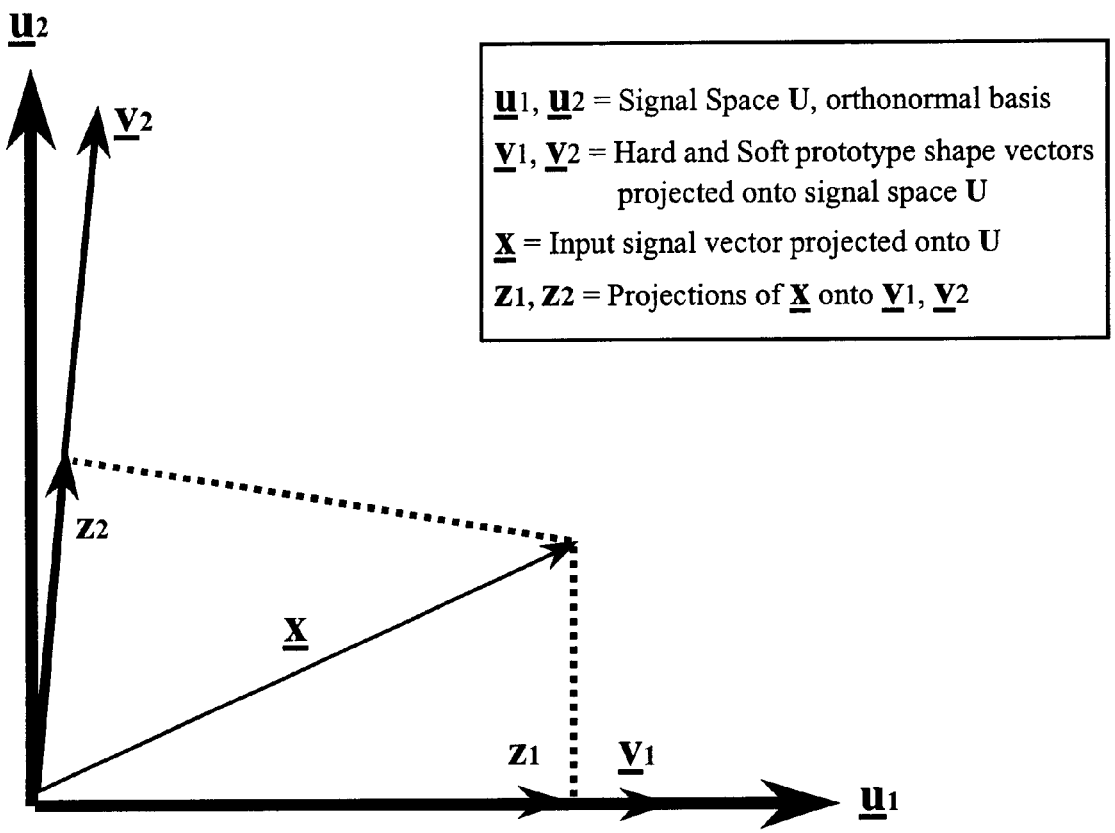
FIG. 2 is a graphical depiction of a matched filter computation as used in the present invention.

Referring now to FIG. 2, a graphical depiction is shown of a matched filter computation as used in the present invention.

The projection of the input vector onto U is accomplished as shown in Equation 2.

$$Z = \begin{bmatrix} Z_1 \\ Z_2 \end{bmatrix} = \begin{bmatrix} (x, v_1) \\ (x, v_2) \end{bmatrix} \quad \text{(Equation 2.)}$$

The vector z is then the projection of the normalized input vector $\underline{x}$ onto the space spanned by the two basis prototype vectors $v_1$ and $v_2$. The detection process performs this matched-filter computation to determine which prototype inclusion class is closest to the normalized input vector $\underline{x}$ and proceeds to output the filter outputs z to the threshold and comparator units. The lengths of $z_1$ and $z_2$ then are input to the threshold logic unit for deciding the presence or absence of soft and hard inclusions.

$$I\begin{bmatrix} t_1 \\ t_2 \\ t_3 \end{bmatrix} = \begin{bmatrix} \{1, \text{if } z_1 \geq T_1, \text{else } 0\} \\ \{1, \text{if } z_1 \geq z_2, \text{else } 0\} \\ \{1, \text{if } z_2 \geq t_2, \text{else } 0\} \end{bmatrix} \quad \text{(Equation 3.)}$$

where T is the binary output vector.

The threshold units have binary output 0, if the match is less than a predetermined threshold, and 1 if the match is greater than or equal to the threshold. The comparator unit outputs a 1 if the wide pulse detection filter is greater than the narrow pulse detection filter. Otherwise it outputs a 0. The binary vector from the threshold and comparator units then is passed to the decision logic unit for final determination of the pulse class from the current input frame. This binary vector is created by the concatenation of each comparator bit. The binary vector then is used as an address to a binary lookup table to read the decision of the pulse shape type. This table serves the purpose of a three-input, two-output Boolean logic function as shown in Equation 4.

(Equation 4.)

| H | | T | | |
|---|---|---|---|---|
| $h_0$ | $h_1$ | $T_1$ | $T_2$ | $T_3$ |
| 0 | 0 | 0 | 0 | 0 |
| 0 | 1 | 0 | 0 | 1 |
| 1 | 0 | 1 | 0 | 0 |
| 0 | 1 | 1 | 0 | 1 |
| 0 | 0 | 0 | 1 | 0 |
| 1 | 0 | 1 | 1 | 0 |
| 1 | 0 | 1 | 1 | 1 | where T is the binary vector containing the outputs from the comparison and threshold units, and h is the decision output vector from the table h=[ho, h1]. ho when 1 indicates the presence of a soft inclusion. h1 when 1 indicates the presence of a hard inclusion. When both ho and h1 are 0, no inclusions are present.

The decision variables ho and h1 then are used to compute the particle size histograms using a class-based counting scheme that computes the number of counts per kilogram of sampled liquid metal. Counts are used subsequently to compute likelihood of occurrence for each particle classification type, both hard and soft inclusion classes. These in turn are displayed on a graphical window on the computer and stored on disk media for further off-line analysis.

EXAMPLE I

An experimental LiMCA II Particle Detector and Classifier system (hardware and software) was tested online. The experimental system was connected to a LiMCA II during a 70 minute casting run. The unit required changes to the pulse detection and classification software. In addition, changes to the user interface were made to make it easier to use. Real-time data from the LiMCA were collected on a digital tape recorder during the run to use in troubleshooting and testing changes to the software. The accuracy of the detection and classification probabilities for the two pulse types was subsequently tested.

EXAMPLE II

A LiMCA II Particle Detector and Classifier (LiMCA PDC) was assembled, and the LiMCA PDC system hardware and software was ported to a Toshiba laptop computer. On-line field tests were performed. As a result of these field tests, several suggestions were made for modifications, enhancements, and simplifications to the user interface software and were subsequently implemented. A macro for Excel spreadsheets also was specified and created that simplified the reading and plotting of output data files from both the LiMCA and LiMCA PDC. The macro enabled the user to select parameters specifying particle size histogram ranges and to select the plotting of counts-per-Kilogram and percentages of hard and soft particles on the same graphs automatically. The field data were used to verify the accuracy of the detection and classification probabilities for the two pulse types.

A potential ground isolation problem was observed between one of the MMP LiMCAs and the analog-digital converter connection in the laptop computer. Only one of the LiMCAs exhibited this problem.

The present invention provides a display and controls graphical user interface GUI screen to summarize data processed by the details of the algorithms and to present a visual display of the summarized data in a suitable operator interface.

Figure 3:
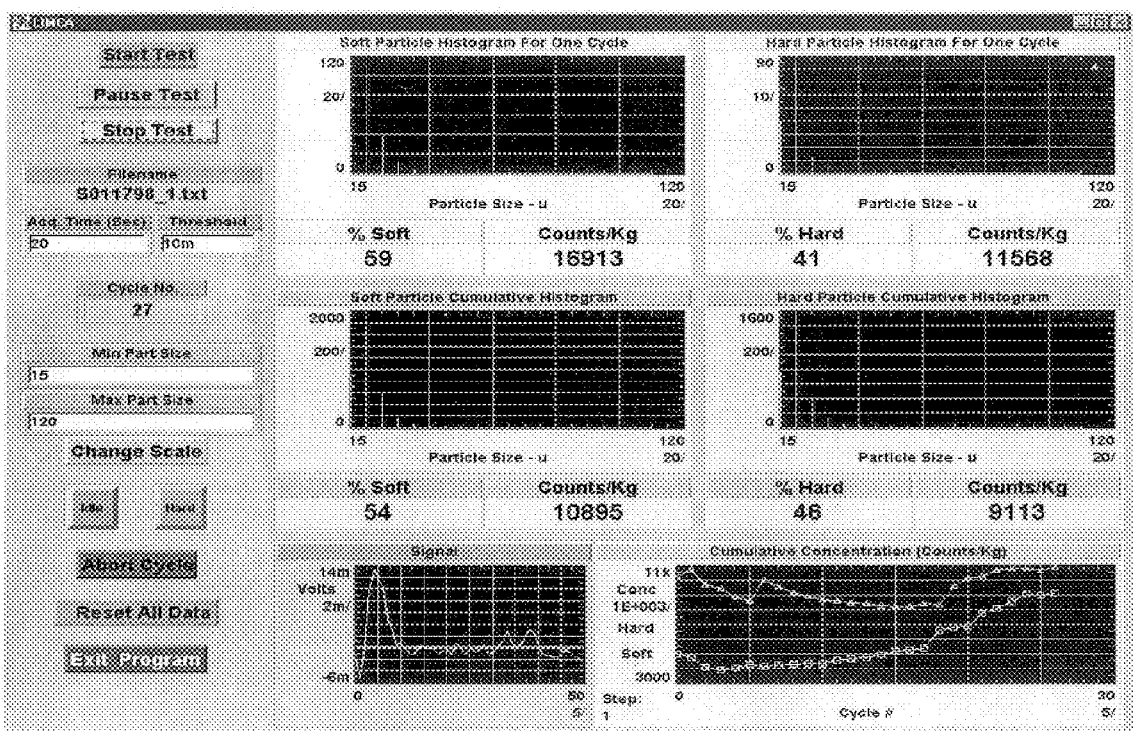
FIG. 3 is a graphical user interface as part of the inclusion particle detection and classifying apparatus and method of the present invention.

Referring now to FIG. 3, a graphical user interface is shown as part of the inclusion particle detection and classifying apparatus and method of the present invention.

The apparatus and method of the present invention preferably employs 5 millisecond intervals to classify a narrower pulse, indicating a hard inclusion. By narrower is meant a pulse width typically less than 1 millisecond. The apparatus and method of the present invention employs the 5 millisecond intervals to classify a wider pulse asa soft inclusion. By wider is meant a pulse width typically greater than 1 millisecond. Some pulses are not narrower or wide. Decisions are made by applying decision logic to the sample.

The LiMCA apparatus is counting voltage pulses of a metal stream passing through an orifice. The apparatus and method of the present invention take the LiMCA output and use a set of Digital Matched Filters for detecting, using statistical detection theory, different signals in a signal stream. The apparatus and method of the present invention work with mathematical components in an inner product computation, looking to determine how close the signals match a specified pattern.

The matched filter of the apparatus and method of the present invention is based on two prototypical shapes, one for a narrow pulse and one for a wide pulse. The two prototypical shapes are used for the basis. The two prototypical shapes are normalized and orthogonalized. By orthogonalized is meant a way of creating a basis, much like the Fourier series and sines and cosines, which are all orthogonal. It is a way of taking a set of arbitrary shapes, which then are made orthogonal, to determine if an unknown shape coming in is closer to one or the other of the two prototypical shapes. If there is a right angle between the two basis shapes, if the input shape vector is closer to one basis vector as opposed to the other, it is suitable to separate the two and make a determination on classification. In this way, the two prototypical shapes are orthogonalized and used as the filter coefficients on a map of the two prototypical shapes. The determination operation is performed on the signal stream coming in, on every 5 millisecond frame, using 10 kilohertz. The apparatus and method of the present invention take the signal vector out of that 5 millisecond frame and compare it to the two prototypical shapes as filter coefficients, as in a pattern matching. The unknown signal is determined as one or the other or neither. If it matches closely to the prototypical hard inclusion pulse, then it is declared to be a hard inclusion. By matching closely is meant the inner product computations performed by the matched filter is close to a +1. Similarly, if it matches closely to the prototypical soft inclusion pulse, then it is declared to be a hard inclusion. A degree of match is anywhere from 0 to 1. It has to be of a sufficient degree, which is greater than a threshold of 0.5. If it is not, the inclusion pulse is not identified as one or the other.

Matched filters refer to looking for a certain pattern in a signal stream, and analysis t match it. It is a computational procedure that tries to a find a match. It acts as a detector for a signal known to be somewhere in a particular signal stream. It tells when the signal is present and to what degree. It is different from the traditional filter for removing noise components from signal stream.

The apparatus and method of the present invention take known pulse shapes, being a function, and turn those into prototypes. A Gramm Schmidt orthogonalization is used to get better separability. For patterns in one space that may be fairly close together, more room, in a sense, is provided to distinguish an unknown between the two, more so than if they are too close together in one space, a non-orthogonal or redundant. That is the purpose of the normalization. When that is done, the two vectors are shown as depicted in FIG. 2. The two prototypical vectors then are projected into the orthonormal basis created in the form of the transformed prototype control. U1 is an x-axis vector. U2 is an orthogonal to U1. All signals are vectors in this signal space. The apparatus and method of the present invention project, onto these control forms, (1) input signals coming in from the signal stream and (2) the original prototype forms that the form was created with, i.e., V1 and V2 near orthogonal and, as projected onto u1 u2 basis, V1 and V2 near orthogonal. Through the inner product computation of the matched filter, the apparatus and method of the present invention take the unknown signal vector coming in from the 5 millisecond frame, project on both the v1 and v2. In two operations, the apparatus and method of the present invention take the prototype vectors, create the orthonormal basis u1 u2, and take those prototypes and project them on to this basis, and gives the v1 and v2.

Then the matched filter processing comes in on the stream such that as a new vector comes in a signal, project that on to v1 v2, and that gives the z1 z2. The length of z1 or z2 determines whether it is closer to v1. As it gets closer to v1, z1 becomes longer. When $\underline{x}$ is equal to v1, z1 will be equal to v1 in length, which is 1, because they are ortho-normalized. In the other case, if they are identical to the other vector, it will be equal to z2, a length 1. In between, these two get longer or shorter, depending on whether it is closer to the other one or not. If closer to v1 than v2, then a wide pulse. Pulse input classification is determined by decision logic using the absolute relative lengths of z1 and z2.

Another vector from the next frame comes in, do the same comparison, and that is how the identification is performed.

Where a decision is required is at the middle, 45 degree angle, a point where it is close to both. Is it one or the other? Not happen very often. A common problem in statistical detection theory, an ambiguity when it is like a short pulse and like a wide pulse. Probability density functions of the two types of pulse make the decision.

The apparatus and method of the present invention look at a pulse, parameterize it, i.e., put it in an equation form, i.e., to draw the curve to create that shape.

The apparatus and method of the present invention look at the data, on the order of about 1 millisecond for the short one (narrower pulse), and about 5 millisecond for the long one (wider pulse),over the 5 millisecond frame for our standard frame length. The apparatus and method of the present invention then put it in Gramm Schmidt ortho-normalization procedure, thereby to create an n-dimensional basis for arbitrary vectors.

The apparatus and method of the present invention take the curve, describe it mathematically, look at actual data such that related distance on the frame to time, put it through ortho-normalization procedure, and get u1 u2 basis vectors to provide the vector representation. The apparatus and method of the present invention then take the prototypes filters or shapes and project them onto the u basis using the inner product computation, thereby to get v1 v2.

By inner product computation is meant, in the theory of vector spaces, operations and vector addition, scalable multiplication, or dot product between two vectors x, which can be function, rays or numbers. In a functional space, x can be functional representation for performing the inner product. In the apparatus and method of the present invention, the numeric representation of the two prototypes is an array of numbers. For vector u, perform an inner product between $\underline{x}$ and give a projection, parameterized and generated onto a prototype mathematically.

In the apparatus and method of the present invention, vector normalizing prevents large swings in amplitude from interfering the identification. Amplitude information nevertheless is maintained to determine size in microns. However, the absolute amplitude is not needed to determine type of pulse.

It has been found that the apparatus and method of the present invention provide information as to which filters to use for correcting specific problems in the molten metal processing, which information as to which filters to use for correcting specific problems in the molten metal processing was not available previously.

It has been found that LiMCA apparatus tubes break easily.

It has been found that with the LiMCA alone, it is important to pay attention to the signal. While looking at very low voltage changes through a low resistance metal such as aluminum at a high current, the LiMCA is very susceptible to noise. With the LiMCA, it is important to pay attention to the signal, particularly in a noise situation. Provision is not made in the instrument for detecting abnormal signals.

It has been found that in the operation of the apparatus and method of the present invention, an interface is needed. Two signals are taken from the LiMCA, one to tell when it is acquiring data and another of the actual analog signal. A ground must be kept separate between the two signals. A grounding system for the analog and the digital are two separate grounding systems.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of determining a classification of inclusion types in molten metal, comprising:
    a. comparing a normalized digital signal vector to a control set of a prototype inclusion shape;
    b. determining a classification of inclusion type for said digital signal vector by decision logic;
    c. determining a shape of said inclusions from said digital signal vector; and
    d. counting said inclusion classification and shape.

2. The method of determining a classification of inclusion types in molten metal as set forth in claim 1 wherein said counting said classification and shape comprises updating a histogram of classified inclusion types.

3. The method of determining a classification of inclusion types in molten metal as set forth in claim 2 further comprising viewing said histogram of classified inclusion types in a graphical user interface.

4. The method of determining a classification of inclusion types in molten metal as set forth in claim 1 wherein said classification of inclusions comprises hard inclusions versus soft inclusions.

5. The method of determining a classification of inclusion types in molten metal as set forth in claim 4 wherein said hard inclusions comprise oxides or other non-deformable particles.

6. The method of determining a classification of inclusion types in molten metal as set forth in claim 4 wherein said soft inclusions comprise salt droplets, gas bubbles, agglomerates of other very small particle types, or other deformable particles.

7. The method of determining a classification of inclusion types in molten metal as set forth in claim 4 comprising using Gram-Schmidt ortho-normalization to form a fundamental basis of control.

8. The method of determining a classification of inclusion types in molten metal as set forth in claim 4 wherein said normalized signal vector is formed by determining a classification for said digital signal vector by passing said normalized signal vector through a decision module comprising at least one threshold unit and at least one digital logic table to make a decision of a soft, deformable inclusion or a hard inclusion.

9. The method of determining a classification of inclusion types in molten metal as set forth in claim 4 wherein said determining a shape of said inclusions by normalized amplitude vector comprises determining voltage amplitude height.

10. The method of determining a classification of inclusion types in molten metal as set forth in claim 4 further comprising providing a grounding system for the analog signal and the digital signal consisting of two separate grounding systems.

11. The method of determining a classification of inclusion types in molten metal as set forth in claim 1 further comprising converting an analog signal stream to a digital signal stream by passing said analog signal stream through an analog to digital converter with subsequent calculation to form said normalized digital signal vector.

12. The method of determining a classification of inclusion types in molten metal as set forth in claim 1 further comprising partitioning said digital signal stream into a discrete time frame of 5 milliseconds.

13. The method of determining a classification of inclusion types in molten metal as set forth in claim 1, wherein said step of comparing said normalized signal vector to a control set of a prototype inclusion shape comprises performing an inner vector product of said signal vector and a control vector indicative of said prototype shape.

14. Apparatus for determining a classification of inclusion types in molten metal, comprising:
   a. means for comparing a normalized signal vector to a control set of a prototype inclusion shape;
   b. a decision module comprising at least one threshold unit and at least one digital logic table for determining a classification for said digital signal vector by decision logic;
   c. means for determining a shape for said inclusions from said normalized amplitude vector; and
   d. means for counting said inclusion classification and size.

15. The apparatus for determining a classification of inclusion types in molten metal as set forth in claim 14 further comprising a grounding system consisting of two separate grounding systems for the analog and digital signal.

16. The apparatus for determining a classification of inclusion types in molten metal as set forth in claim 14 further comprising a graphical user interface for viewing a histogram of classified inclusion types.

17. The apparatus for determining a classification of inclusion types in molten metal as set forth in claim 14 wherein said classification of inclusions comprises hard inclusions versus soft inclusions.

18. The apparatus for determining a classification of inclusion types in molten metal as set forth in claim 14 wherein said hard inclusions comprise oxides or other non-deformable particles.

19. The apparatus for determining a classification of inclusion types in molten metal as set forth in claim 14 wherein said soft inclusions comprise salt droplets, gas bubbles, agglomerates of other very small particle types, or other deformable particles.

20. The apparatus for determining a classification of inclusion types in molten metal as set forth in claim 14 further comprising partitioning said digital signal stream into a discrete time frame of 5 milliseconds.

21. A method of determining a classification of inclusion types in molten metal, comprising:
   a. obtaining an analog signal stream from a Coulter counter apparatus;
   b. passing said analog signal stream through an analog to digital converter to convert said analog signal stream to a digital signal stream;
   c. partitioning said digital signal stream into a discrete time frame of 5 milliseconds;
   d. vector normalizing said digital signal stream to provide a normalized signal vector;
   e. comparing said normalized signal vector to a control set of prototype inclusion shape;
   f. determining a classification for said digital signal vector by decision logic to determine hard inclusions versus soft inclusions by passing said normalized signal vector through a decision module comprising at least one threshold unit and at least one digital logic table to make a decision of a soft, deformable inclusion or a hard inclusion;
   g. determining a shape for said inclusions by normalized amplitude vector;
   h. counting said inclusion classification and shape and updating a histogram of classified inclusion types; and
   i. viewing said histogram of classified inclusion types in a graphical user interface.

* * * * *